(12) United States Patent
Simpson

(10) Patent No.: US 7,654,979 B2
(45) Date of Patent: Feb. 2, 2010

(54) BALLOON CATHETER HAVING IMPROVED BALLOON SEAL

(75) Inventor: John Arthur Simpson, Carlsbad, CA (US)

(73) Assignee: Advanced Cardiovascular System, Inc., Santa Clara, CA (US)

( * ) Notice: Subject to any disclaimer, the term of this patent is extended or adjusted under 35 U.S.C. 154(b) by 612 days.

(21) Appl. No.: 11/022,494

(22) Filed: Dec. 21, 2004

(65) Prior Publication Data

US 2006/0135982 A1 Jun. 22, 2006

(51) Int. Cl.
*A61M 29/00* (2006.01)
(52) U.S. Cl. ....................... 604/103; 606/192
(58) Field of Classification Search ........... 604/533, 604/523, 264, 96.01, 93.01, 48, 19, 101.01–103.14; 606/192–196
See application file for complete search history.

(56) References Cited

U.S. PATENT DOCUMENTS

| | | | |
|---|---|---|---|
| 3,884,242 A | 5/1975 | Bazell et al. | |
| 4,301,803 A | 11/1981 | Handa et al. | |
| 4,406,653 A | 9/1983 | Nunez | |
| 5,108,416 A * | 4/1992 | Ryan et al. | 606/194 |
| 5,195,972 A * | 3/1993 | Inoue | 604/103 |
| 5,697,946 A * | 12/1997 | Hopper et al. | 606/185 |
| 5,868,704 A * | 2/1999 | Campbell et al. | 604/103.11 |
| 5,876,376 A | 3/1999 | Schwab et al. | |
| 6,187,013 B1 | 2/2001 | Stoltze et al. | |
| 6,699,273 B2 * | 3/2004 | Langan | 623/1.11 |
| 6,723,113 B1 * | 4/2004 | Shkolnik | 606/194 |
| 6,841,029 B2 * | 1/2005 | Lim | 156/308.6 |
| 6,923,827 B2 * | 8/2005 | Campbell et al. | 623/1.11 |
| 6,939,321 B2 * | 9/2005 | Wang et al. | 604/103.08 |
| 6,946,173 B2 * | 9/2005 | Lim et al. | 428/35.2 |
| 6,982,024 B2 * | 1/2006 | Shkolnik | 156/293 |
| 7,011,646 B2 * | 3/2006 | Blankenship | 604/103.06 |
| 7,025,745 B2 * | 4/2006 | Lim et al. | 604/103.06 |
| 2004/0062890 A1 | 4/2004 | Wang et al. | |
| 2004/0127850 A1 * | 7/2004 | Steadham et al. | 604/103 |

* cited by examiner

*Primary Examiner*—Matthew F Desanto
(74) *Attorney, Agent, or Firm*—Fulwider Patton LLP

(57) ABSTRACT

The end cap is preferably formed of a relatively high durometer material with an inner surface on an outer surface of the shaft and on an outer surface of the balloon skirt section, and contacts a compression member on the balloon outer surface. The configuration prevents or inhibits failure at the balloon seals which otherwise results from the compression member moving or the balloon pulling off the shaft and out from under the compression member during inflation of the balloon. As a result, the balloon catheter of the invention has an improved consistent burst pressure and/or failure mode.

20 Claims, 3 Drawing Sheets

BALLOON CATHETER HAVING IMPROVED BALLOON SEAL

This invention relates generally to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter must have good crossability (i.e., the ability of the catheter distal end to cross stenosed portions of the vascular anatomy).

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which instead readily expand to the working diameter within the patient's body lumen from a generally cylindrical or tubular shape that conforms to the catheter shaft (i.e., with essentially no folded wings).

Catheter balloons formed of expanded polytetrafluoroethylene (ePTFE) expanded in place within the patient's body lumen without blow molding the ePTFE tubing have been disclosed. Prior disclosed methods of forming the ePTFE balloon involve heat fusing a wrapped sheet of ePTFE to form an ePTFE tube and joining the ePTFE tube to a nonporous second layer to form the balloon. However, one difficulty has been securely attaching the ePTFE balloon to the catheter shaft.

Accordingly, it would be a significant advance to provide a catheter with an improved strong bond between the balloon and catheter shaft without disadvantageously affecting catheter performance. This invention satisfies these and other needs.

SUMMARY OF THE INVENTION

The invention is directed to a balloon catheter having an end cap encircling an end of the balloon. The end cap is preferably formed of a relatively high durometer material with an inner surface on an outer surface of the shaft and on an outer surface of the balloon skirt section, and contacts a compression member on the balloon outer surface. The configuration prevents or inhibits failure at the balloon seals which otherwise results from the compression member moving or the balloon pulling off the shaft and out from under the compression member during inflation of the balloon. As a result, the balloon catheter of the invention has an improved consistent burst pressure and/or failure mode.

The catheter generally comprises an elongated shaft having an inflation lumen and a guidewire lumen, and a balloon on a distal shaft section with a proximal skirt section and a distal skirt section secured to the shaft so that an interior chamber of the balloon is in fluid communication with the inflation lumen. The balloon catheter can be configured for a variety of medical procedures including dilatation or stent delivery.

In a presently preferred embodiment, the balloon has a proximal compression member on an outer surface of the balloon proximal skirt section, and a distal compression member on an outer surface of the balloon distal skirt section. However, in alternative embodiments, the balloon has only one of the proximal or the distal compression member. The compression member is preferably a band, although a variety of suitable alternative compression members can be used including a coil. The compression member is typically formed of a metallic material such as stainless steel, radiopaque alloys, or a shape memory or superelastic alloy such as Nitinol. The compression member may alternatively be formed of a high strength plastic. In a presently preferred embodiment, the compression member is a swaged metallic band. Swaging as used herein refers to the method of applying radially compressing force uniformly around the entire circumference of an object. Thus, unlike crimping in which a radially compressive force is applied merely at intermittent points around the circumference, a swaged member provides a uniform sealing force around the entire circumference of the swaged band.

Preferably, the proximal compression member has a proximal end located distal to a proximal end of the balloon proximal skirt section. As a result, the proximal skirt section has a segment extending proximally beyond the proximal compression member. Similarly, the distal compression member preferably has a distal end located proximal to a distal end of the balloon distal skirt section, so that the distal skirt section has a segment extending distally beyond the distal compression member.

In accordance with the invention, an end cap is provided on one or both ends of the balloon. Specifically, in a presently preferred embodiment, a proximal end cap encircles the proximal end of the balloon proximal skirt section. In addition to or instead of the proximal end cap, the balloon catheter similarly has a distal end cap which encircles the distal end of the balloon distal skirt section. The end caps are typically in contact with the compression members, and in a presently preferred embodiment abut an end of the compression member. The end cap has a maximum outer diameter that is preferably not greater than the outer diameter of its associated compression member, so that the end cap does not increase the profile of the catheter beyond the profile otherwise formed at the compression member. Similarly, the end cap preferably does not extend along an inner or outer surface of the compression member. However, in less preferred embodiments in which the profile is increased by the end cap, the end cap has a section which extends along an inner or outer surface of the compression member.

The end cap is preferably formed of a relatively high durometer adhesive. The adhesive bonds directly to the outer surface of the shaft and the balloon. Additionally, applied as a liquid adhesive and cured on the catheter, the adhesive has an excellent ability to be shaped so that the end cap has the desired dimensions.

The features of the invention can prove particularly useful with catheters having balloons formed of various low durometer materials. The seals at either end of such balloons are prone to failure at least in part because the low durometer material does not possess adequate strength to resist tearing or the peel loading that occurs upon balloon inflation. The end cap is sized so that the compression member (e.g., a seal band) cannot ride over it. Additionally, the end cap is preferably of a sufficient hardness that when axial force is applied to the compression member by the balloon during inflation, the compression member is unable to displace the end cap. The end cap bonded to the shaft thus serves as a buttress to carry axial seal band loads.

Additionally, a balloon catheter having the balloon bonded in accordance with the invention has a decreased risk of the compression member becoming separated from the balloon catheter. Dislodgment of the compression member is a significant and potentially deadly problem. For example, if the balloon fails during inflation in a patient's body lumen due to the balloon skirt sections pulling out from under the compression members, or if the compression member otherwise becomes dislodged, the compression member could become separated from the balloon catheter and left behind in the patient's body lumen. Therefore, providing a consistent failure mode which avoids dislodgement of the compression member is a significant advantage.

In a presently preferred embodiment, the balloon has a first layer of a porous polymeric material such as expanded polytetrafluoroethylene (ePTFE) and a second layer of a low durometer elastomeric material. The elastomeric, second layer is nonporous, so that the balloon inflates by retaining inflation fluid within the interior chamber of the balloon. Although discussed herein in terms of a presently preferred embodiment in which the porous polymeric layer is an outer layer relative to the nonporous layer, it should be understood that the porous polymeric layer is an inner layer in an alternative embodiment. In a presently preferred embodiment, the porous polymeric layer is impregnated, along at least a section thereof, with a polymeric material which at least partially fills the pores of the porous polymeric material. In one embodiment, the nonporous layer is omitted and the porous polymeric layer is sufficiently impregnated with a polymeric material to reduce the fluid-permeability of the porous polymeric material so that the balloon is inflatable.

A variety of suitable porous polymers may be used to form the porous polymeric layer of the balloon, including expanded polytetrafluoroethylene (ePTFE), an ultra high molecular weight polyolefin such as ultra high molecular weight polyethylene (UHMWPE), porous polyethylene, porous polypropylene, and porous polyurethane. In a presently preferred embodiment, the porous polymeric material has a node and fibril microstructure. For example, ePTFE and UHMWPE (also known as expanded UHMWPE), typically has a node and fibril microstructure comprising nodes interconnected by fibrils. ePTFE and UHMWPE are typically formed into a balloon layer by heat fusing helically wrapped sheets of the material together into a tubular shape.

A method of making a balloon catheter embodying features of the invention generally comprises bonding a proximal skirt section and a distal skirt section of a balloon to a catheter shaft so that the balloon has an interior in fluid communication with an inflation lumen of the shaft, radially collapsing a proximal compression member on an outer surface of the proximal skirt section of the balloon bonded to the shaft, and dispensing a liquid adhesive at the proximal end of the proximal skirt section of the balloon and curing the adhesive to form a proximal end cap at the proximal end of the balloon proximal skirt section. The proximal end of the proximal compression member is preferably located distal to the proximal end of the balloon, so that the balloon proximal skirt section has a segment extending proximally beyond the proximal compression member. The proximal end cap has an inner surface preferably on an outer surface of the shaft and on an outer surface of the extending segment (i.e., the segment which extends proximally beyond the proximal compression member) of the balloon proximal skirt section. Although discussed above in terms of a proximal compression member and end cap on the balloon proximal skirt section, it should be understood that the invention alternatively or additionally has a distal compression member and end cap on the balloon distal skirt section.

Balloon catheters of the invention have a relatively high rated burst pressure (i.e., calculated from the average rupture pressure, it is the pressure at which 95% of the balloons can be pressurized to without rupturing). The balloon catheters have at least one end cap configured to contribute to providing a relatively strong balloon seal, and preferably without causing a disadvantageously stiff or large profile catheter distal end. Additionally, the configuration of the balloon bonded section(s) in accordance with the invention provides a more consistent failure mode which decreases the risk of the compression member becoming separated from the balloon catheter. These and other advantages of the invention will become more apparent from the following detailed description and exemplary drawings.

DETAILED DESCRIPTION OF THE PREFERRED EMBODIMENTS

Figure 1:
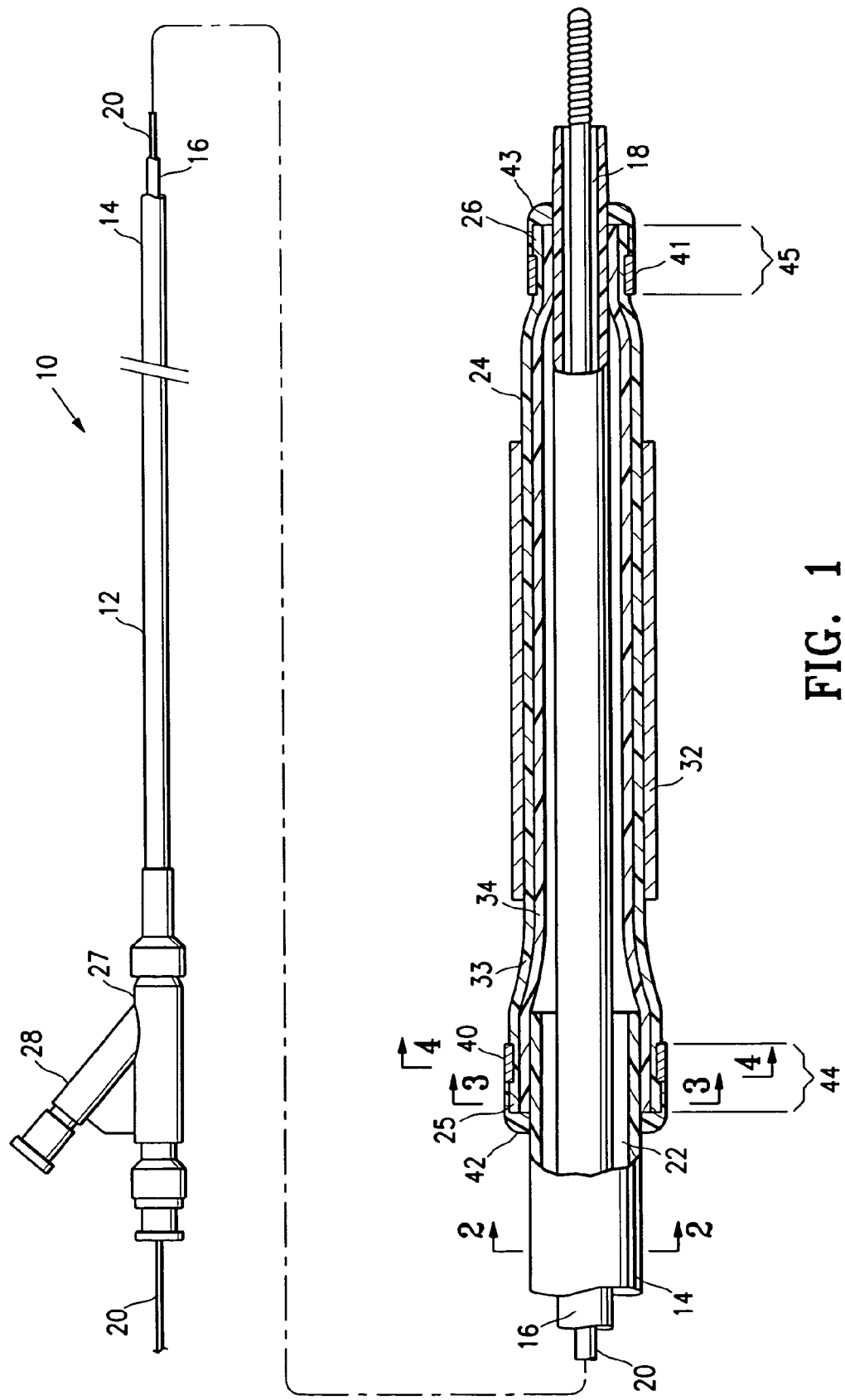
FIG. 1 is an elevational view partially in section of a balloon catheter embodying features of the invention.
Figure 2:
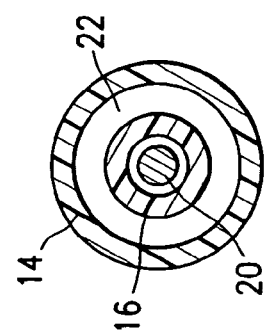
FIGS. 2-4 are transverse cross sectional views of the balloon catheter of FIG. 1, taken along lines 2-2, 3-3, and 4-4, respectively.
Figure 3:
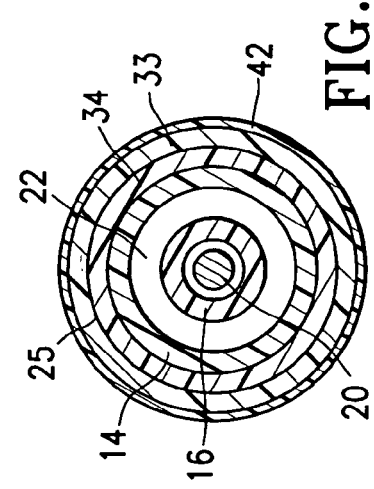
Figure 4:
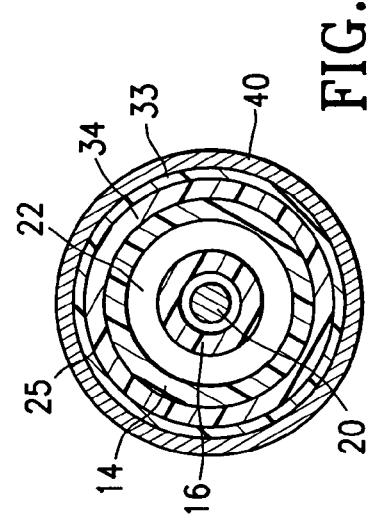

FIG. 1 illustrates an over-the-wire type stent delivery balloon catheter 10 embodying features of the invention. Catheter 10 generally comprises an elongated catheter shaft 12 and an inflatable balloon 24 on a distal shaft section. In the illustrated embodiment, the shaft comprises an outer tubular member 14 defining an inflation lumen 22 therein, and an inner tubular member 16 defining a guidewire lumen 18 therein configured to slidingly receive a guidewire 20. Specifically, in the illustrated embodiment, the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2-2. In the embodiment illustrated in FIG. 1, the guidewire lumen 18 extends to the proximal end of the catheter. Inflatable balloon 24 has a proximal skirt section 25 sealingly secured to the distal end of outer tubular member 14 and a distal skirt section 26 sealingly secured to the distal end of inner tubular member 16, so that the balloon interior chamber is in fluid communication with inflation lumen 22. An adapter 27 at the proximal end of catheter shaft 12 is configured to provide access to guidewire lumen 18, and to direct inflation fluid through arm 28 into inflation lumen 22.

Figure 5:
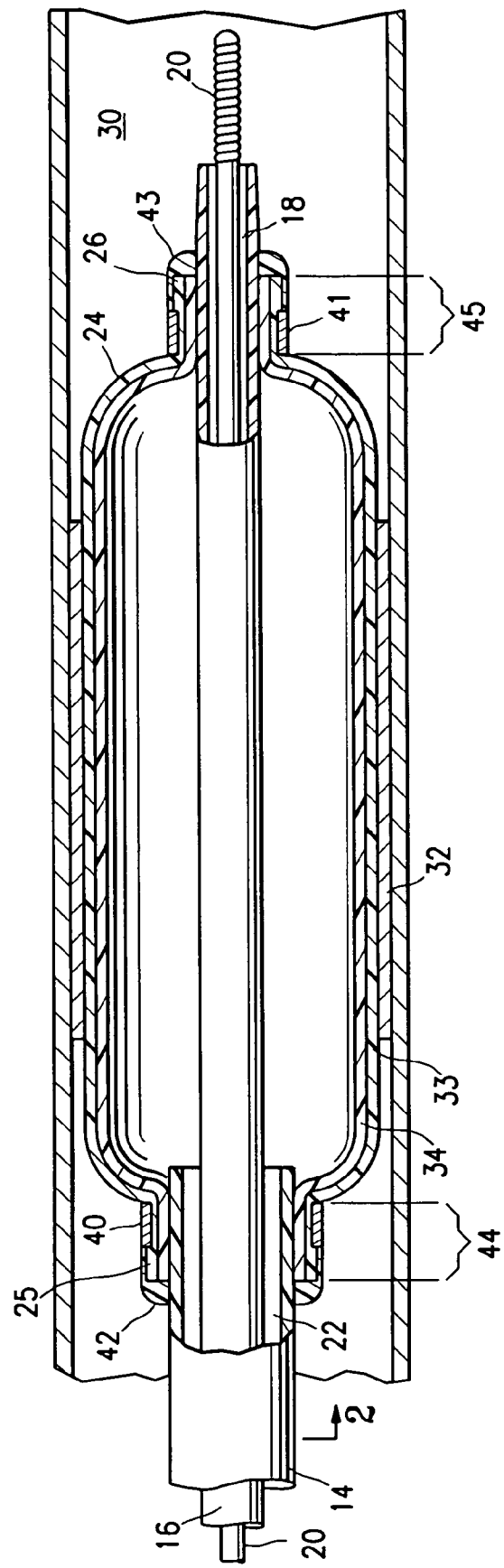
FIG. 5 illustrates the balloon of FIG. 1 in an inflated configuration.

The balloon 24 is illustrated in FIG. 1 in a noninflated configuration prior to complete inflation thereof. In the embodiment of FIG. 1, balloon 24 has an essentially wingless noninflated configuration. However, in alternative embodiments (not shown), the balloon has a noninflated configuration with folded wings wrapped around the catheter. The distal end of catheter 10 may be advanced to a desired region of the patient's body lumen in a conventional manner with the balloon 24 in a noninflated configuration, and the balloon 24 inflated by directing inflation fluid into the balloon interior, to perform a medical procedure such as dilatation or delivery of a stent. In the embodiment illustrated in FIG. 1, an expandable stent 32 is mounted on the working length of the balloon 24 for delivery and deployment within a patient's body lumen 30. FIG. 5 illustrates the balloon in an inflated configuration which expands the stent 32 into place against the body lumen wall.

Figure 1A:
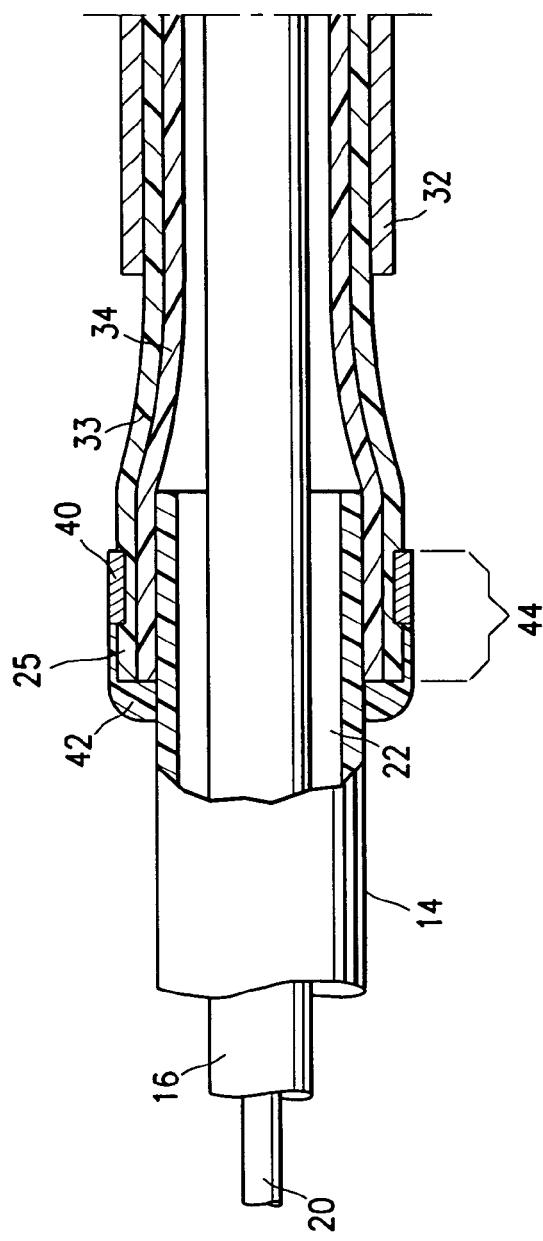
FIG. 1A is an enlarged partial view of the balloon catheter of the FIG. 1, illustrating the proximal end of the balloon.

The balloon 24 has an outer layer 33 and an inner layer 34 extending the full length of the balloon, from the proximal skirt section 25 to the distal skirt section 26. The inner surface of the outer layer 33 is preferably bonded to the inner layer 34, as for example by fusion bonding and/or adhesive bonding. At least a portion of the balloon 24 proximal and distal skirt sections 25, 26 are bonded to the shaft 12, preferably by fusion and/or adhesive bonding. In the embodiment illustrated in FIG. 1, the proximal skirt section 25 extending along the outer tubular member 14 has a bonded portion 44 (bonded to the outer surface of the outer tubular member) and, preferably, a nonbonded portion (not bonded to the outer tubular member) distal to bonded portion 44. Similarly, the distal skirt section 26 has a bonded portion 45 (bonded to the outer surface of the inner tubular member). FIG. 1A illustrates an enlarged view of the proximal end of the balloon catheter of FIG. 1.

The balloon catheter 10 has a proximal compression member 40 which in the embodiment of FIG. 1 is a swaged band on an outer surface of the balloon proximal skirt section 25, and a distal compression member 41 which is similarly a swaged band on an outer surface of the balloon distal skirt section 26. Although illustrated as bands 40, 41, it should be understood that alternative compression members may be used. The swaged band compression members 40, 41 preferably are a metallic material, such as stainless steel or a Tantalum-based or a Platinum-based radiopaque alloy.

The distal end of the proximal swaged band 40 is preferably radially aligned (within manufacturing tolerances) with the distal end of the bonded portion 44 of the proximal skirt section 25 for improved seal strength. The proximal end of the proximal swaged band 40 is located distal to a proximal end of the balloon proximal skirt section 25, so that the proximal skirt section 25 has a segment extending proximally beyond the proximal swaged band 40. Similarly, the distal swaged band 41 preferably has a proximal end radially aligned (within manufacturing tolerances) with the proximal end of the bonded portion 45 of the distal skirt section 26. The distal end of the distal swaged band 41 is located proximal to a distal end of the balloon distal skirt section 26, so that the distal skirt section 26 has a segment extending distally beyond the distal swaged band 41. In one embodiment (not shown), the swaged bands 40, 41 have one or more holes extending through the side wall from an outer to an inner surface of the bands to provide a passage for adhesive during bonding of the bands 40, 41 to the underlying balloon.

A proximal end cap 42 encircles the proximal end of the balloon proximal skirt section 25, and a distal end cap 43 encircles the distal end of the balloon distal skirt section 26. The proximal end cap 42 has an inner surface on an outer surface of the shaft outer tubular member 14 and on an outer surface of the extending segment of the balloon proximal skirt section 25. Similarly, the distal end cap 43 has an inner surface on an outer surface of the shaft inner tubular member 16 and on an outer surface of the extending segment of the balloon distal skirt section 26.

The ends of the proximal and distal end caps 42, 43 abut (i.e., contact) the respective compression members 40, 41. As a result, the end caps 42, 43 do not extend along an inner or outer surface of the compression members. Specifically, the proximal end cap 42 has a distal end abutting the proximal end of the proximal compression member 40, and the distal end cap 43 has a proximal end abutting the distal end of the distal compression member 41. In the illustrated embodiment, the proximal and distal end caps 42, 43 each have a maximum outer diameter which is equal to the outer diameter of the respective compression member 40, 41 (i.e., the end caps are flush with the respective compression member).

In one embodiment (not shown) the compression members 40, 41 have a notched or otherwise irregularly outer edge which, encased by the end caps 42, 43, improves the anchoring of the compression members 40, 41 by the end caps 42, 43. For example, in one embodiment (not shown), the end cap has tabs extending from the outer edge which can be bent inward and that become completely encased by the end cap.

Thus, a distal end section of the proximal end cap encases the tabs extending from the outer (i.e., proximal) edge of the proximal compression member and abuts the proximal end of the rest of the proximal compression member which sealingly surrounds the shaft. Because the tabs can be bent inwardly, extending the end cap over and around them does not increase the profile beyond the profile otherwise formed at the compression member. Additionally, in one embodiment, the outer surface of the extending segment of the balloon skirt section is chemical solution-etched to improve bondability.

The end caps 42, 43 are typically formed of a material which is different from the balloon material(s), and which has a higher Shore durometer hardness than the balloon material (s). In a presently preferred embodiment, the end caps 42, 43 are formed of a relatively high durometer adhesive. The adhesive typically has Shore durometer hardness of at least about 65D, and more preferably of at least about 72D. For example, Loctite 4304, 4305, 4306 and 4307 are UV-cure, dual-mode curing (i.e., light and moisture-curing) cyanoacrylate adhesives having a durometer after curing of about 72D. The adhesive bonds directly to the outer surface of the shaft and balloon. However, in alternative embodiments, the end cap is formed of alternative, but similarly high durometer, materials such as a polymer sleeve of a thermoplastic polymer that is adhered by fusion bonding.

Balloon outer layer 33 preferably comprises a microporous polymeric material having a node and fibril microstructure such as ePTFE. Although discussed below primarily in terms of the embodiment in which the outer layer 33 is ePTFE, it should be understood that a variety of suitable materials can be used to form outer layer 33. The inner layer 34 is formed of a polymeric material preferably different from the polymeric material of the outer layer 33, and in a presently preferred embodiment is an elastomeric nonporous layer. Inner layer 34 limits or prevents leakage of inflation fluid through the microporous ePTFE to allow for inflation of the balloon 24. The inner layer 34 is preferably formed of an elastomeric material to facilitate deflation of the balloon 24 to a low profile deflated configuration, including polyurethanes, silicone rubbers, polyamide block copolymers, dienes, and the like. Inner layer 34 may consist of a separate layer which neither fills the pores nor disturbs the node and fibril structure of the ePTFE layer 33, or it may at least partially fill the pores of the ePTFE layer 33. The Shore durometer hardness of the balloon layer 34 is typically relatively low. For example, the elastomeric material of the balloon inner layer 34 has a Shore durometer hardness of typically about 70 Shore A to about 100 Shore A, which is significantly less than that of the material of the end caps 42, 43. The Shore durometer hardness of the material of balloon outer layer 33 is similarly significantly less than the Shore durometer hardness of the material of the end caps 42, 43. End caps formed of a material having a Shore durometer of about 64D or less do not have the required strength to prevent failure at the balloon seals during inflation of the balloon to inflation pressures above about 300 psi.

The ePTFE layer 33 is preferably formed according to a method in which ePTFE polymeric material is wrapped with overlapping or abutting edges and then heated to fuse the wrapped material together into a tubular shape. The resulting tube of ePTFE polymeric material is typically further processed by being stretched, heat treated, compacted, and heat treated again, to provide the desired properties such as the desired dimension, and dimensional stability (i.e., to minimize changes in length occurring during inflation of the balloon). The completed ePTFE layer 33 is then bonded to or otherwise combined with elastomeric liner 34 either before or after layer 34 is bonded to the shaft.

In a method of making a balloon catheter embodying features of the invention, the proximal skirt section is bonded to the outer surface of the shaft outer tubular member 14. Specifically, in a presently preferred embodiment, the proximal skirt section 25 is bonded to the shaft by applying heat and a radially compressive force to at least a portion of the length of the skirt section 25 which extends along the outer tubular member 14, which heats the material of the inner layer 34 to effect a bond to the underlying portion of the shaft. The resulting bonded length 44 typically has a reduced outer diameter as illustrated in FIG. 1, so that an external shoulder is formed in the balloon outer layer 34 at the end of the bonded portion 44 of the skirt section 25. The radially compressive force is preferably applied using a press having a collapsible faceted bore configured to receive the balloon skirt section therein. Although not illustrated, a tie layer may be provided between the balloon inner layer 34 and the shaft, with a length about equal to the bonded portion 44, to facilitate bonding the inner layer 34 to the shaft. For example, a fusion-bonded or adhesive-bonded tie layer formed of a polyurethane is preferably provided between a polyurethane inner layer 34 and a polyamide outer tubular member 14. The distal skirt section 26 is similarly bonded to the outer surface of the shaft inner tubular member 16.

The method includes radially collapsing, e.g., swaging, the proximal compression member 40 on an outer surface of the proximal skirt section 25 of the balloon bonded to the shaft, with the compression member 40 proximal end preferably being located distal to a proximal end of the balloon proximal skirt section 25 so that the proximal skirt section 25 has a segment extending beyond the proximal compression member 40. The compression members 40, 41 are radially collapsed to a sufficiently small diameter to achieve an interference fit with the balloon skirt section, i.e., a smaller inner diameter than the outer diameter of the skirt section prior to application of the compression member. As a result, at least a portion of a wall thickness of the compression member is embedded in the balloon, and generally about 25% to about 75% of the wall thickness is embedded. In the embodiment illustrated in FIG. 1, about 50% of the wall thickness of the proximal compression member 40 is embedded into the balloon proximal skirt section 25.

The end caps 42, 43 are then applied to the ends of the balloon 24. Preferably, a liquid adhesive is dispensed on the proximal end of the proximal skirt section 25 and cured to form a proximal end cap 42 encircling the proximal end of the balloon proximal skirt section 25. The distal end cap 43 is similarly formed.

The embodiment of the balloon catheter having the end caps located over the extending segment of the balloon skirt section and in contact with the compression member have an increased rupture pressure compared to a balloon catheter having the compression member end aligned with the end of the balloon (i.e., so that the balloon skirt sections do not have extending segments). Specifically, in the later case, the proximal and distal seals will fail at lower inflation pressures due to the balloon skirt section pulling off the shaft and out from under the compression member. The length of the extending segment of the balloon skirt sections is typically about 0.1 mm to about 1 mm, and more preferably about 0.3 mm to about 0.7 mm (or 0.5 mm ±0.2 mm), and is typically about 5% to about 60%, more specifically about 15% to about 40% of a total length of the balloon skirt section. The length of the extending segment is minimized to minimize the increase in the catheter stiffness caused by the extending segment and overlying end cap. The length of the extending segment required to prevent balloon failure at the balloon seal during inflation to a desired inflation pressure depends on factors such as the amount of interference (i.e., depth that the compression member is compressed down into the balloon skirt section) between the compression member and the balloon skirt section.

Balloon catheters having 3.0 mm OD balloons with swaged band compression members and end caps formed of Loctite 4304 (with a cured Shore durometer hardness of about 72D) were prepared and inflated to test the rupture characteristics. The balloons had a mean rupture pressure of about 382 psi, and a standard deviation of about 28 psi. None of the balloons having a 0.5 mm extending segment and a 72D end cap failed by one of the balloon skirt sections pulling out from under the compression member. In contrast, about one quarter of the balloons similarly formed but without the extending segment failed due to one of the balloon skirt sections pulling out from under the compression member. The balloons bonded to the shaft in accordance with the invention had a more consistent failure mode and one which, importantly, prevents or decreases the risk of the compression member becoming separated from the balloon catheter. Additionally, when compared to balloons having softer end caps, the balloons had a higher consistent burst pressure. Specifically, balloons having the 0.5 mm extending segment but with softer end caps (formed of Loctite 3311, with a cured Shore durometer hardness of about 64D) had a lower mean rupture pressure of about 317 psi, and a standard deviation of about 58 psi.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 5 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire type balloon catheter, the catheter of this invention may comprise a variety of intravascular catheters, such as a rapid exchange type balloon catheter. Rapid exchange catheters generally comprise a shaft having a relatively short guidewire lumen extending from a guidewire distal port at the catheter distal end to a guidewire proximal port spaced a relatively short distance from the distal end of the catheter and a relatively large distance from the proximal end of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A balloon catheter, comprising:
   a) an elongated shaft having an inflation lumen and a guidewire lumen;
   b) a balloon on a distal shaft section, having a proximal and distal skirt section with at least a portion secured to the shaft so that an interior chamber of the balloon is in fluid communication with the inflation lumen;
   c) a proximal compression member on an outer surface of the balloon proximal skirt section, having a proximal end located distal to a proximal end of the balloon proximal skirt section, so that the proximal skirt section has an extending segment which extends proximally beyond the proximal compression member; and the extending segment has an inner surface bonded to the shaft; and
   d) a proximal end cap encircling the proximal end of the balloon proximal skirt section, the end cap having an inner surface on an outer surface of the shaft and on an outer surface of the extending segment of the balloon proximal skirt section, and a distal end that extends no further then the proximal compression member.

2. The balloon catheter of claim 1 including a distal compression member on an outer surface of the balloon distal skirt section, with a distal end located proximal to a distal end of the balloon distal skirt section, so that the distal skirt section has a segment extending distally beyond the distal compression member, and a distal end cap encircling the distal end of the balloon distal skirt section, the distal end cap having an inner surface on an outer surface of the shaft and on an outer surface of the extending segment of the balloon distal skirt section.

3. The balloon catheter of claim 2 wherein the balloon distal skirt section has a bonded portion secured to the shaft, and the distal compression member has a proximal end radially aligned with a proximal end of the bonded portion of the balloon distal skirt section.

4. The balloon catheter of claim 1 wherein the proximal compression member has an inner diameter which is less than an outer diameter of the balloon proximal skirt section, so that at least a portion of a wall thickness of the proximal compression member is embedded in the balloon.

5. The balloon catheter of claim 4 wherein about 25% to about 75% of the wall thickness of the proximal compression member is embedded in the balloon.

6. The balloon catheter of claim 1 wherein the end cap has a distal-most end abutting a proximal end of the compression member, so that the end cap does not extend along an inner or outer surface of the compression member.

7. The balloon catheter of claim 1 wherein the end cap has a maximum outer diameter which is not greater than the maximum outer diameter of the compression member.

8. The balloon catheter of claim 1 wherein the end cap has a maximum outer diameter which is equal to the maximum outer diameter of the compression member.

9. The balloon catheter of claim 1 wherein the balloon is formed of one or more polymeric materials, and the end cap is formed of a material which is different than the balloon materials and which has a higher Shore durometer hardness than the balloon materials.

10. The balloon catheter of claim 1 wherein the end cap is formed of an adhesive which has a Shore durometer hardness of at least about 65D.

11. The balloon catheter of claim 1 wherein the balloon proximal skirt section has a bonded portion secured to the shaft and a nonbonded portion not bonded to the shaft, and the proximal compression member has a distal end radially aligned with a distal end of the bonded portion of the balloon proximal skirt section.

12. The balloon catheter of claim 1 wherein the balloon proximal skirt section has a bonded portion secured to the shaft and a nonbonded portion not bonded to the shaft, and the proximal compression member has a distal end located closer to a distal end than to a proximal end of the bonded portion of the balloon proximal skirt section.

13. The balloon catheter of claim 1 wherein the proximal compression member is selected from the group consisting of a metallic band, a shape memory band, a superelastic band, a swaged band, and a coil.

14. The balloon catheter of claim 1 wherein the extending segment of the balloon proximal skirt section has a length of about 0.1 to about 1.0 mm.

15. The balloon catheter of claim 1 wherein the outer surface of the extending segment of the balloon proximal skirt section is chemical solution-etched.

16. The balloon catheter of claim 1 wherein the balloon skirt section is bonded to a tie layer on the shaft, formed of a material configured to bond to the inner surface of the inner layer of balloon and to the outer surface of the shaft such that the tie layer facilitates bonding the balloon to the shaft.

17. The balloon catheter of claim 1 wherein the balloon comprises a first layer of porous polymeric material selected from the group consisting of expanded polytetrafluoroethylene, ultra high molecular weight polyolefin, porous polyethylene, porous polypropylene, and porous polyurethane, and a second layer of a nonporous elastomeric material.

18. A balloon catheter, comprising:
a) an elongated shaft having an inflation lumen and a guidewire lumen;
b) a balloon on a distal shaft section, having a proximal and distal skirt section with at least a portion secured to the shaft so that an interior chamber of the balloon is in fluid communication with the inflation lumen, and having an outer layer of expanded polytetrafluoroethylene material and an inner layer of elastomeric material bonded to the outer layer;
c) a proximal metallic band on an outer surface of the balloon proximal skirt section, having a proximal end located distal to a proximal end of the balloon proximal skirt section so that the proximal skirt section has a segment extending proximally beyond the proximal metallic band, and a proximal end cap encircling the proximal end of the balloon proximal skirt section with a distal-most end which abuts and which is flush with a proximal end of the proximal metallic band, the proximal end cap having an inner surface on an outer surface of the shaft and on an outer surface of the extending segment of the balloon proximal skirt section; and
d) a distal metallic band on an outer surface of the balloon distal skirt section, having a distal end located proximal to a distal end of the balloon distal skirt section, so that the distal skirt section has a segment extending distally beyond the distal metallic band, and a distal end cap encircling the distal end of the balloon distal skirt section with a proximal end which abuts and which is flush with a distal end of the distal metallic band, the distal end cap having an inner surface on an outer surface of the shaft and on an outer surface of the extending segment of the balloon distal skirt section.

19. The balloon catheter of claim 18 wherein the end caps are formed of an adhesive having a Shore durometer hardness which is higher than a Shore durometer hardness of the balloon materials and which is at least about 65D.

20. A balloon catheter, comprising:
a) an elongated shaft having an inflation lumen and a guidewire lumen;
b) a balloon on a distal shaft section, having a proximal and distal skirt section with at least a portion secured to the shaft so that an interior chamber of the balloon is in fluid communication with the inflation lumen;
c) a proximal compression member on an outer surface of the balloon proximal skirt section, having a proximal end located distal to a proximal end of the balloon proximal skirt section, so that the proximal skirt section has a segment which extends proximally beyond the proximal compression member and which has an inner surface bonded to the shaft; and
d) a proximal end cap encircling the proximal end of the balloon proximal skirt section, the end cap having an inner surface on an outer surface of the shaft and on an outer surface of the extending segment of the balloon proximal skirt section, wherein the end cap has a distal-most end abutting a proximal end of the compression member, so that the end cap does not extend along an inner or outer surface of the compression member.

* * * * *